United States Patent [19]

Neubauer et al.

[11] Patent Number: 5,752,915
[45] Date of Patent: May 19, 1998

[54] DEVICE FOR MANIPULATING A STYLET UNIT FOR POSITIONING A MEDICAL ELECTRODE CABLE IN A BODY CAVITY

[75] Inventors: Heinz Neubauer, Järfälla; Mats Boström, Sundbyberg, both of Sweden

[73] Assignee: Pacesetter AB, Solna, Sweden

[21] Appl. No.: 732,815

[22] Filed: Oct. 15, 1996

[30] Foreign Application Priority Data

Oct. 18, 1995 [SE] Sweden .................. 9503647

[51] Int. Cl.⁶ .................................................. A61B 5/04
[52] U.S. Cl. ................... 600/373; 600/374; 600/585; 606/129; 607/122
[58] Field of Search .................... 128/642, 772, 128/639; 604/280, 282; 606/129; 401/88, 92; 607/116, 119, 122; 600/373, 374, 585

[56] References Cited

U.S. PATENT DOCUMENTS

| | | |
|---|---|---|
| 4,136,703 | 1/1979 | Wittkampf ............. 128/772 |
| 4,509,945 | 4/1985 | Kramann et al. |
| 4,601,599 | 7/1986 | Katoh ............. 401/99 |
| 5,170,787 | 12/1992 | Lindegren et al. ............. 128/642 |
| 5,267,982 | 12/1993 | Sylvanowicz ............. 604/280 |
| 5,397,321 | 3/1995 | Houser et al. ............. 606/41 |
| 5,465,733 | 11/1995 | Hinohara et al. ............. 128/772 |

*Primary Examiner*—Lee S. Cohen
*Assistant Examiner*—David M. Ruddy
*Attorney, Agent, or Firm*—Hill & Simpson

[57] ABSTRACT

A device for manipulating a stylet unit for positioning an electrode cable in a body cavity has an elongate housing, an elongate, axial cavity in the housing and an operating slide, axially movable in relation to the housing, for attachment to a proximal end section of a tubular stylet sleeve in a stylet unit. An elongate coil spring is located in the cavity on the proximal side of the manipulation device. The coil spring forms an inner guide channel to prevent the buckling of the free, proximal end section of the stylet of the stylet unit in the cavity.

16 Claims, 1 Drawing Sheet

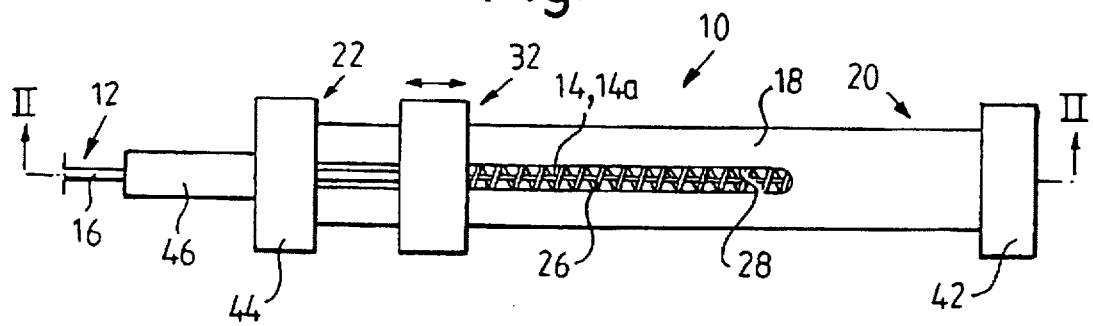
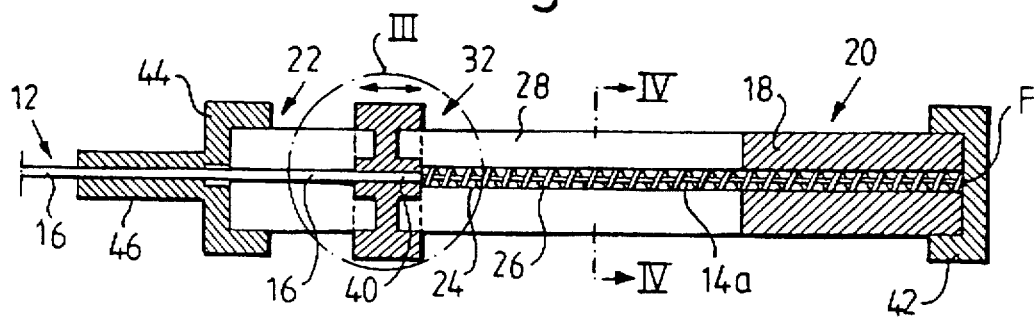
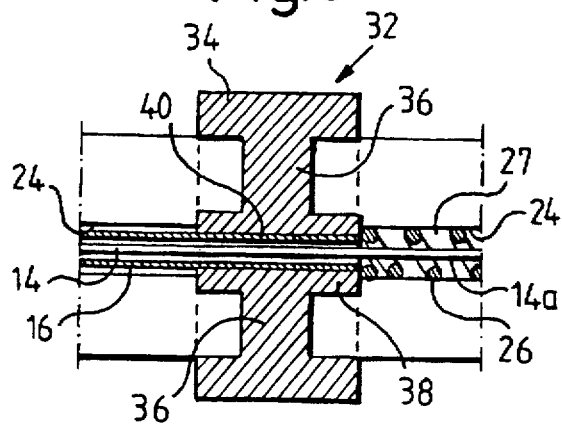
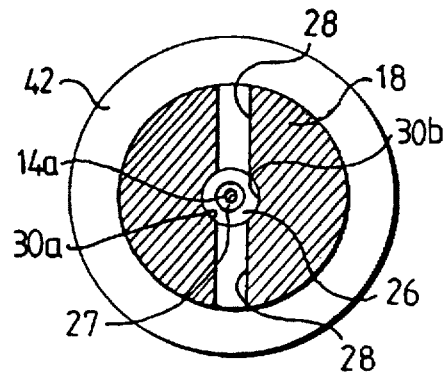

DEVICE FOR MANIPULATING A STYLET UNIT FOR POSITIONING A MEDICAL ELECTRODE CABLE IN A BODY CAVITY

BACKGROUND OF THE INVENTION

1. Field of the Invention

The present invention relates to a device for manipulating a stylet unit for positioning an electrode cable in a body cavity, the device being of the type containing an elongate housing with a proximal end and a distal end section, an elongate axial cavity in the housing and an operating slide, axially movable in relation to the housing for connection to a proximal end section of a tubular stylet sleeve of the stylet unit.

2. Description of the Prior Art

U.S. Pat. No. 5,170,787 describes a device for manipulating a stylet unit in order to achieve a desired stiffening of an electrode cable during its advancement into a body cavity, e.g. through a vein into the atrium of a heart, and to achieve a desired final positioning of the distal end of the electrode cable by giving it an L or J shape. The stylet unit used for this purpose consists of an inner stylet enclosed in a tubular stylet sleeve. The distal end of the stylet is pre-curved. The distal end is kept retracted inside the stylet sleeve during the introduction of the electrode cable into the body cavity in order to keep the distal end of the electrode substantially straight. The stylet is deployed out of its tubular sleeve, when the distal end of the electrode cable is to be placed in its final position, to bend the distal end of the electrode cable into the desired curved shape. In order to achieve deployment of the pre-curved distal end of the stylet out of the tubular sleeve, this patent proposes a device which either pushes the stylet out in a distal direction in relation to the stationary tubular sleeve or slides the tubular sleeve in a proximal direction in relation to the stationary stylet. The latter version is preferable, since there is then no displacement of the electrode cable in relation to the stylet's manipulation device. The known manipulation device contains two stiff, telescoping tubes to provide non-buckling stiffening of the stylet when the proximal end of the manipulation device is slid distally into the tubular sleeve or when the tubular sleeve is slid proximally over the free proximal end of the stylet in the manipulation device. This means that the manipulation device is relatively long, since the total length of the telescoping tubes must be twice the length of the stylet's stroke movement in relation to its tubular sleeve.

SUMMARY OF THE INVENTION

An object of the present invention is to provide a manipulation device, of the general type initially described above, with a much shorter length and fewer components than the aforementioned prior art manipulation device.

For this purpose the manipulation device according to the invention has an elongate cavity devised to enclose, with a tight fit, an elongate coil spring on the proximal side of the operating slide. The spring forms an inner, axial guide channel to prevent a free, proximal end section of a stylet of the stylet unit in the cavity from buckling when the proximal end section of the stylet sleeve is slid over the free proximal end section of the stylet with the aid of the operating slide while shortening the length of the spring. Since the stiff, telescoping tubes in the known design have been replaced by stylet-supporting, compressible coil spring the total length of the manipulation device can be greatly shortened, and the number of parts in the manipulation device can be reduce, thereby making it cheaper to manufacture.

DESCRIPTION OF THE DRAWINGS

FIG. 1 is a side view of a stylet manipulation device according to the present invention.

FIG. 2 is a sectional view of the manipulation device taken along line 11—11 in FIG. 1.

FIG. 3 is an enlarged sectional view of the circular area III in FIG. 2.

FIG. 4 is a sectional view taken along line IV—IV in FIG. 2.

DESCRIPTION OF THE PREFERRED EMBODIMENTS

FIGS. 1 and 2 show a manipulation device, generally designated 10, for a stylet unit, for achieving a desired stiffening of an electrode cable (not shown) during its introduction into a body cavity, e.g. through a vein in the right atrium of the heart, and for positioning the distal end of the electrode cable in a desired manner against the heart wall for fixation of the end there. The manipulation device 10 is intended for manipulating a stylet unit 12 of the kind containing an internal stylet 14 (shown most clearly in FIG. 3) and a tubular sleeve 16 enclosing same, both the sleeve 16 and the stylet 14 being intended for introduction inside the central channel of an electrode cable to stiffen the cable during its introduction. This stylet unit 12 is designed to bend the distal end of the electrode cable into e.g. a J shape when the cable reaches its final position. For this purpose, the distal end of the internal stylet 12 is precurved in a known manner, but it is kept enclosed inside the tubular sleeve 16 during the introduction of the electrode cable, thereby keeping the distal end section of the stylet unit 12, and accordingly the electrode cable, essentially straight. When the distal end of the electrode cable has been advanced e.g. into the right atrium of the heart, the tubular stylet sleeve 16 can be retracted, whereupon the pretensioning of the curved, exposed distal end section of the stylet 14 bends the flexible, distal end section of the electrode cable into the desired L or J shape. The manipulation device 10 according to the invention is therefore designed to control the movement of the tubular sleeve 16 in relation to the stylet 14. The device 10 has an elongate cylindrical housing 18 with a proximal end section 20 and a distal end section 22. A cavity in the form of a channel or hole 24, devised to admit the stylet sleeve 16, containing the stylet 14, with a tight fit, passes through the center of the housing 18, as well as through a coil spring 26. A free, proximal end section 14a of the stylet passes through a guide channel 27 in the spring 26 (FIG. 4) to an attachment point F (FIG. 2) on the proximal end section 20 of the housing 18.

The housing 18 has an elongate axial slot 28 which passes diametrically through the hole 24 (FIG. 4), the hole 24 in this slotted section of the housing 18 then being limited by two opposing, semicylindrical walls 30a and 30b. As shown in greater detail in FIG. 3, an operating slide 32 is arranged to move axially along the housing 18 and has a ring collar 34 which is connected to a hub section with two diametrically opposed radial pins 36 which pass through the slot 28, the proximal end 40 of the tubular sleeve 16 being affixed to this hub section.

In one embodiment, the coil spring 26 is a compression spring whose proximal end rests against or is mounted on a proximal end section 42 affixed to the proximal end 20 of the housing 18. The distal end of the coil spring 26 presses against the proximal end section 40 of the tubular sleeve 16 and/or against the hub section of the operating slide which affixes the end section 40. Alternatively, the spring 26 can be of a tension spring whose ends are mounted on the end section 42 and tubular sleeve 16 or hub section 38.

An end section 44 is mounted on the distal end 22 of the housing 18 and has an axial, distally projecting shaft journal 46. A known sleeve (not shown) can be mounted on the journal 46 and can be connected to a contact pin on the proximal end of the electrode cable to permit rotation of the cable during active fixation of the cable's distal end.

The manipulation device 10 according to the invention operates in the following manner. Before the electrode cable is introduced into the body cavity, the stylet unit 12 is fully inserted into the electrode cable with the stylet 14 enclosed by the tubular sleeve 16, i.e. the operating slide 32 is kept in a forward, distal end position in the housing 18. When the distal end of the tubular sleeve 16 reaches the distal end of the electrode cable, the latter can be advanced into the body cavity, e.g. the right atrium of the heart. After it reaches the atrium, the distal end section of the electrode cable is bent into the desired L or J shape when the physician manually retracts the operating slide with his/her fingers 32 in the proximal direction, such that the slide 32 moves the tubular sleeve 16 and exposes the pre-curved distal end of the stylet 14 which accordingly bends the end of the electrode cable into the desired shape, depending on how much the curved distal end of the stylet is exposed. When the spring 26 is a tension spring, the spring 26 tries to contract, thereby facilitating movement thereof in the proximal direction. When the spring 26 is a compression spring, the spring 26 is compressed by the operating slide 32. In both instances, the primary task of the spring 26 is to enclose, with a tight fit, or "brace" the proximal end section 14a of the stylet 14, thereby keeping this free end section 14a from being buckled by the stylet 14 because of friction between the stylet 14 and the sleeve 16. As a result of this shortening of the length of the spring 26, the total length of the manipulation device 10 can be kept relatively short.

When the distal end of the electrode cable reaches its final position, it can be actively affixed to the heart wall by manual rotation of a rotation sleeve (not shown) mounted on the shaft journal to which the electrode cable's proximal contact pin is affixed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode positioning device comprising:
   a medical electrode cable having an interior channel a stylet unit having a tubular stylet sleeve with a stylet movable therein, said stylet having a stylet end section and said stylet sleeve having a stylet sleeve end section, said stylet unit being removably insertable into said channel for positioning the electrode cable in a body cavity
   an elongate housing having first end section and a second end section and an elongate axial cavity in said elongate housing extending between said first and second end sections and surrounding a portion of said stylet unit;
   an operating slide axially movable relative to said elongate housing and connected to said stylet sleeve end section for advancing and retracting said stylet sleeve relative to said stylet; and
   elongate coil spring means, tightly enclosed in said elongate axial cavity and having an inner, axial guide channel in which said stylet end section is received, for preventing said stylet end section from buckling as said operating slide is moved for retracting said stylet sleeve end section over said stylet end section while shortening a length of said coil spring means.

2. A device as claimed in claim 1, wherein said coil spring means comprises a compression spring.

3. A device as claimed in claim 2, wherein said compression spring has a first end and wherein said first end of said compression spring is connected to said first end section of said elongate housing.

4. A device as claimed in claim 3, wherein said compression spring has a second end, opposite said first end, which presses against said stylet sleeve end section.

5. A device as claimed in claim 3, wherein said operating slide has a hub section, and wherein said compression spring has a second end, opposite said first end, which presses against said hub section.

6. A device as claimed in claim 1, wherein said coil spring means comprises a tension spring.

7. A device as claimed in claim 6, wherein said tension spring has a first end and wherein said first end of said tension spring is connected to said first end section of said elongate housing.

8. A device as claimed in claim 7, wherein said tension spring has a second end, opposite said first end, which presses against said stylet sleeve end section.

9. A device as claimed in claim 7, wherein said operating slide has a hub section, and wherein said tension spring has a second end, opposite first end, which presses against said hub section.

10. A device as claimed in claim 1, wherein said elongate housing has an axial, elongate slot connecting said elongate axial cavity in said elongate housing to an exterior of said housing.

11. A device as claimed in claim 10 wherein said axial elongate cavity comprises a cylindrical hole in said first end section of said elongate housing and two opposed semi-cylindrical surfaces in said elongate housing.

12. A device as claimed in claim 10 wherein said operating slide has at least one radially extending pin slidable in said axial elongate slot.

13. A device as claimed in claim 12 wherein said operating slide comprises manipulation means connected to said radially extending pin and movably journaled on an exterior of said elongate housing for moving said operating slide.

14. A device as claimed in claim 13 wherein said manipulation means comprises a ring-shaped element.

15. A device as claimed in claim 1 further comprising a shaft, adapted for connection to said electrode cable, axially projecting from said second end section of said elongate housing for rotating said electrode cable.

16. A device as claimed in claim 1 wherein said first end section of said elongate housing has a fixed portion, wherein said coil spring means has a first end, wherein said stylet end section has a first end, and wherein the respective first ends of said coil spring means and said stylet end section are attached to said fixed portion of said first end section of said elongate housing.

* * * * *